United States Patent
Fan et al.

(10) Patent No.: US 9,084,884 B2
(45) Date of Patent: Jul. 21, 2015

(54) METHOD FOR MAKING PACEMAKER ELECTRODE LEAD

(75) Inventors: Li Fan, Beijing (CN); Wen-Mei Zhao, Beijing (CN); Liang Liu, Beijing (CN); Yu-Quan Wang, Beijing (CN); Li Qian, Beijing (CN); Chen Feng, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 238 days.

(21) Appl. No.: 13/527,780

(22) Filed: Jun. 20, 2012

(65) Prior Publication Data

US 2013/0104396 A1     May 2, 2013

(30) Foreign Application Priority Data

Oct. 28, 2011 (CN) .......................... 2011 1 0333554

(51) Int. Cl.
  *H01R 43/00* (2006.01)
  *A61N 1/05* (2006.01)
  *B82Y 10/00* (2011.01)

(52) U.S. Cl.
  CPC .................. *A61N 1/056* (2013.01); *B82Y 10/00* (2013.01); *Y10T 29/49204* (2015.01)

(58) Field of Classification Search
  CPC .............................. A61N 1/0529; A61N 1/057
  USPC .................. 29/592.1, 825, 828, 868, 874; 174/102 R, 103, 106 R; 607/118–119, 607/116, 122
  See application file for complete search history.

(56) References Cited

U.S. PATENT DOCUMENTS

| | | | |
|---|---|---|---|
| 5,713,945 A | 2/1998 | Fischer et al. | |
| 7,493,160 B2 | 2/2009 | Weber et al. | |
| 7,512,447 B2 | 3/2009 | Marshall et al. | |
| 7,596,415 B2 | 9/2009 | Brabec et al. | |
| 7,750,240 B2 * | 7/2010 | Jiang et al. | 174/102 R |
| 8,574,393 B2 * | 11/2013 | Jiang et al. | 156/311 |
| 8,583,259 B2 * | 11/2013 | Liu et al. | 607/119 |
| 2004/0051432 A1 | 3/2004 | Jiang et al. | |
| 2009/0062895 A1 | 3/2009 | Stahmann et al. | |
| 2009/0194313 A1 | 8/2009 | Jiang et al. | |
| 2009/0255706 A1 | 10/2009 | Jiang et al. | |
| 2010/0147829 A1 | 6/2010 | Liu et al. | |
| 2011/0026758 A1 | 2/2011 | Wang et al. | |
| 2012/0053649 A1 | 3/2012 | Liu et al. | |
| 2012/0271394 A1 | 10/2012 | Foster et al. | |
| 2013/0110212 A1 * | 5/2013 | Feng et al. | 607/119 |

FOREIGN PATENT DOCUMENTS

| | | |
|---|---|---|
| CN | 1484275 | 3/2004 |
| CN | 1943805 | 4/2007 |
| CN | 101499331 | 8/2009 |
| CN | 101757723 | 6/2010 |

(Continued)

*Primary Examiner* — Minh Trinh
(74) *Attorney, Agent, or Firm* — Novak Druce Connolly Bove + Quigg LLP (57) ABSTRACT

The present disclosure relates to a method for making a pacemaker electrode lead. In the method, the conductive wire structure and the carbon nanotube structure are provided. A conductive material is combined with the carbon nanotube structure to form a carbon nanotube composite structure. The carbon nanotube composite structure is covered on surface of the conductive wire structure to form a conductive wire composite structure.

18 Claims, 9 Drawing Sheets (56) References Cited

FOREIGN PATENT DOCUMENTS

| CN | 101925379 | 12/2010 |
|----|-----------|---------|
| CN | 101927057 | 12/2010 |
| CN | 101990147 | 3/2011 |
| TW | 200945372 | 11/2009 |
| TW | 201039670 | 11/2010 |
| TW | I345792 | 7/2011 |

* cited by examiner

METHOD FOR MAKING PACEMAKER ELECTRODE LEAD

CROSS-REFERENCE TO RELATED APPLICATIONS

This application claims all benefits accruing under 35 U.S.C. §119 from China Patent Application No. 201110333554.X, filed on Oct. 28, 2011, in the China Intellectual Property Office, the contents of which are hereby incorporated by reference. This application is related to common-assigned applications entitled, "ELECTRODE LEAD OF PACEMAKER AND PACEMAKER USING THE SAME," on Jun. 20, 2012, and application Ser. No. 13/527,782; "ELECTRODE LEAD OF PACEMAKER AND PACEMAKER USING THE SAME" filed on Jun. 20, 2012, 2011, and application Ser. No. 13/527,784; "PACEMAKERS AND PACEMAKER LEADS" filed on Jun. 20, 2012, and application Ser. No. 13/527,792; "PACEMAKERS AND PACEMAKER LEADS" filed on Jun. 20, 2012, and application Ser. No. 13/527,801; "ELECTRODE LEAD OF PACEMAKER AND PACEMAKER USING THE SAME" filed on Jun. 20, 2012, and application Ser. No. 13/527,780; "ELECTRODE LEAD OF PACEMAKER AND PACEMAKER USING THE SAME" filed on Jun. 20, 2012, and application Ser. No. 13/527,820; "PACEMAKER ELECTRODE LEAD AND PACEMAKER USING THE SAME" filed on Jun. 20, 2012, and application Ser. No. 13/527,836; "PACEMAKER ELECTRODE LEAD AND PACEMAKER USING THE SAME" filed on Jun. 20, 2012, and application Ser. No. 13/527,849.

BACKGROUND

1. Technical Field

The present disclosure relates to a method for making pacemaker electrode lead.

2. Description of Related Art

A pacemaker is an implantable electronic treatment instrument. The pacemaker can deliver an electrical impulse to stimulate an organ having abnormal electrical signals, by which the abnormal organ can be treated.

The pacemaker includes an impulse generator and an electrode lead. The impulse generator is electrically connected with the electrode lead. The electrode lead includes a lead wire and an electrode tip. The lead wire includes a plurality of metal wires. The electrode tip is disposed on an end of the lead wire away from the impulse generator and electrically connected with the metal wires. However, the lead wire composed of the metal wires has poor strength and ductility, and is easily broken due to repeat distortions. Thus, the lifetime of the pacemaker is decreased.

What is needed, therefore, is to provide a method for making a pacemaker electrode lead having high strength and excellent ductility.

BRIEF DESCRIPTION OF THE DRAWINGS

Many aspects of the present disclosure can be better understood with reference to the following drawings. The components in the drawings are not necessarily to scale, the emphasis instead being placed upon clearly illustrating the principles of the present embodiments.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
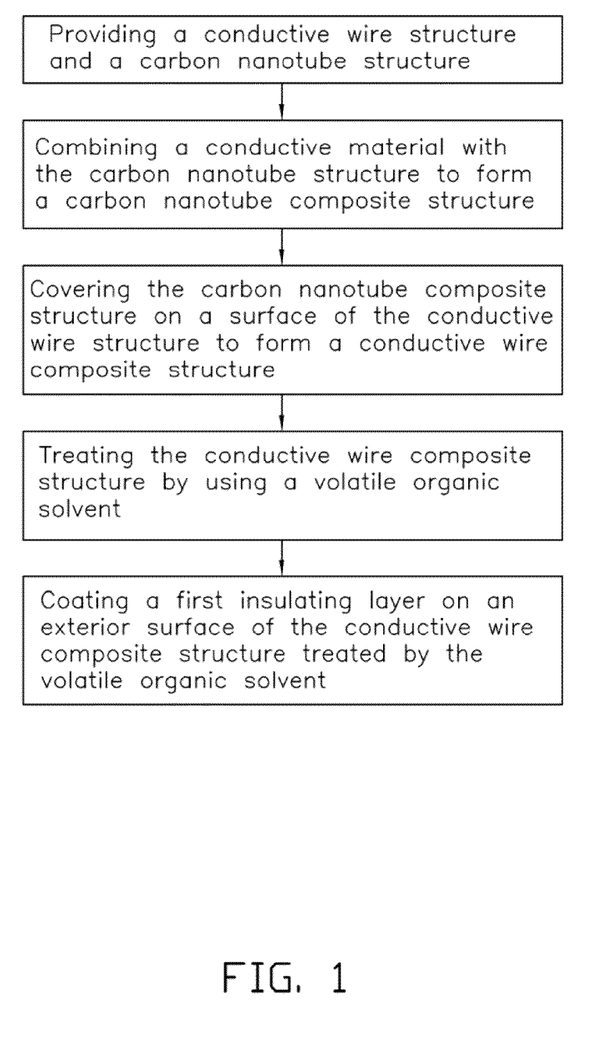
FIG. 1 is a flowchart of one embodiment of a method for making one embodiment of a pacemaker electrode lead.

Referring to FIGS. 1 to 6, one embodiment of a method for making a pacemaker electrode lead 100 includes the steps of:

S1, providing a conductive wire structure 10 and a carbon nanotube structure 12;

S2, combining a conductive material with the carbon nanotube structure 12 to form a carbon nanotube composite structure 14;

S3, covering the carbon nanotube composite structure 14 on a surface of the conductive wire structure 10 to form a conductive wire composite structure 16;

S4, treating the conductive wire composite structure 16 by using a volatile organic solvent; and S5, coating a first insulating layer 18 on an exterior surface of the conductive wire composite structure 16 treated by the volatile organic solvent.

In the above steps, step S4 is optional.

Figure 2:
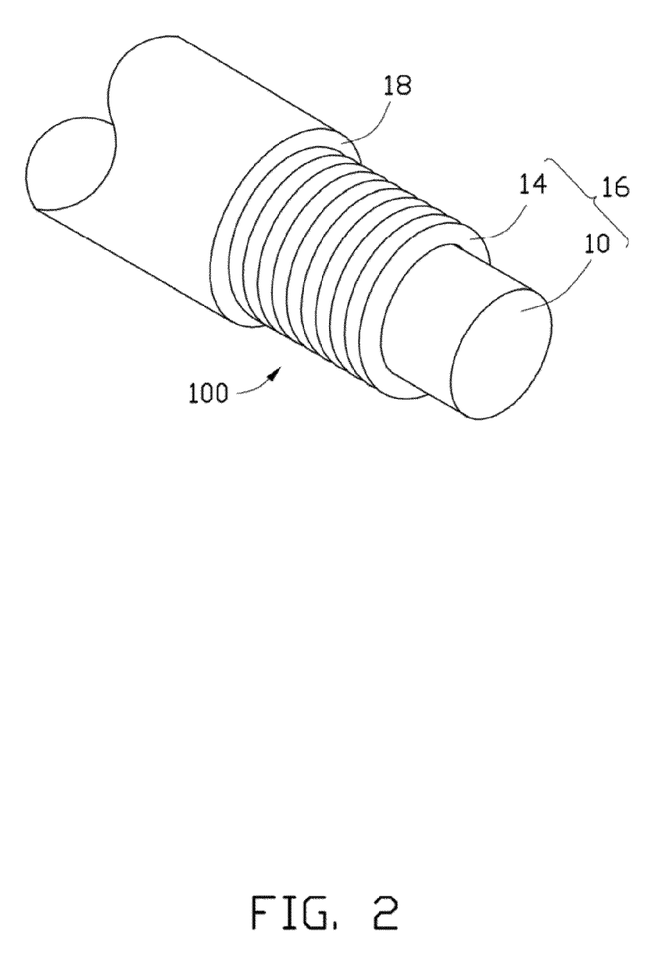
FIG. 2 is a schematic view of the pacemaker electrode lead made by the method of FIG. 1.

In step S1, the conductive wire structure 10 is conductive and can support the carbon nanotube composite structure 14. A material of the conductive wire structure 10 has excellent strength, ductility, and conductivity, and can be made of conductive material, such as stainless steel, carbon fiber, tantalum (Ta), titanium (Ti), zirconium (Zr), niobium (Nb), titanium alloy, copper (Cu), Aurum (Au), silver (Ag), platinum (Pt), platinum yttrium alloy, and platinum palladium alloy. The conductive wire structure 10 can be a hollow cylindrical structure or a solid columnar structure. The hollow cylindrical structure can be formed by the steps of: compactly winding a linear conductive wire on a surface of a wire-shaped support in a helix; and removing the wire-shaped support. A diameter of the conductive wire structure 10 can be in a range from about 1 millimeter (mm) to about 5 mm. In one embodiment, the diameter of the conductive wire structure 10 is in a range from about 2 mm to about 3 mm.

Figure 3:
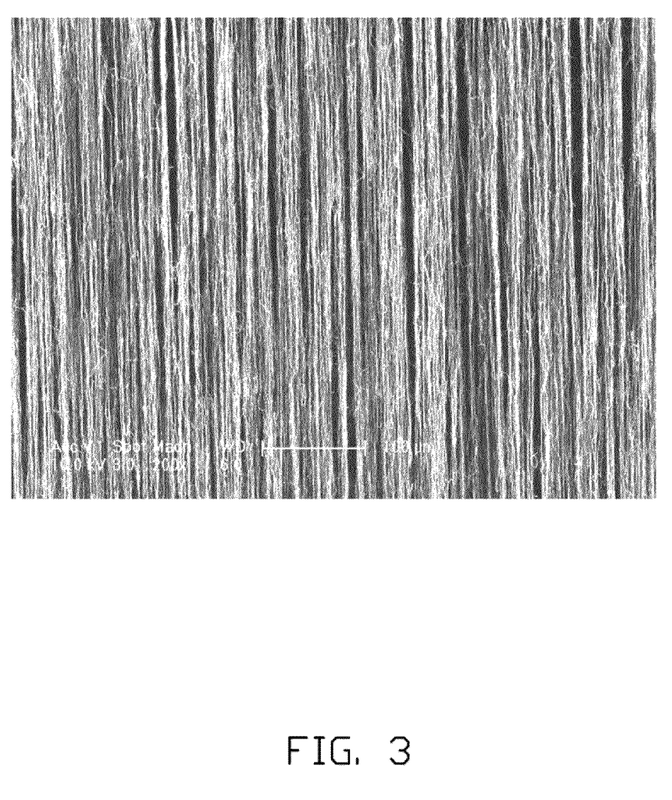
FIG. 3 is a scanning electron microscope (SEM) image of a carbon nanotube drawn film.
Figure 4:
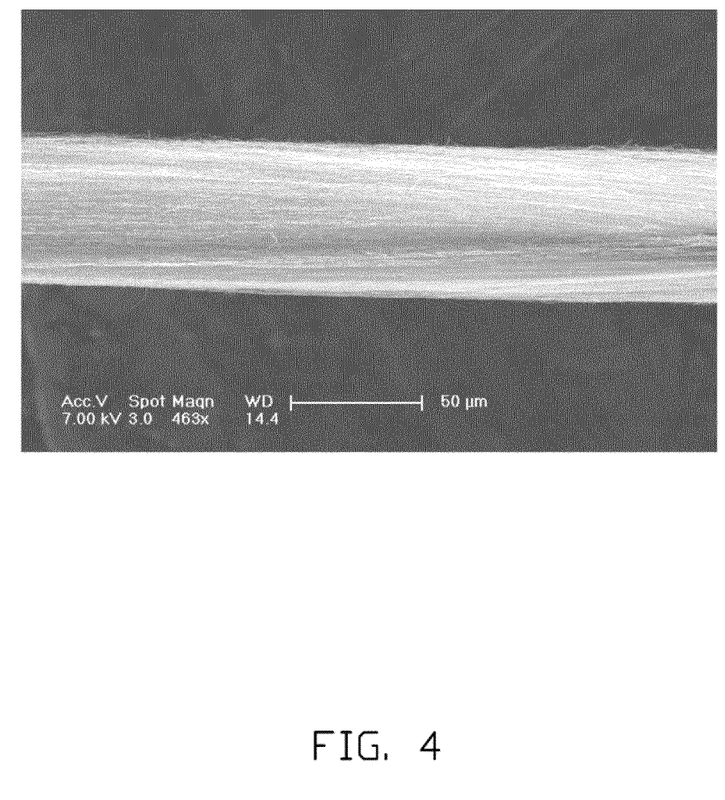
FIG. 4 is a SEM image of a non-twisted carbon nanotube wire.
Figure 5:
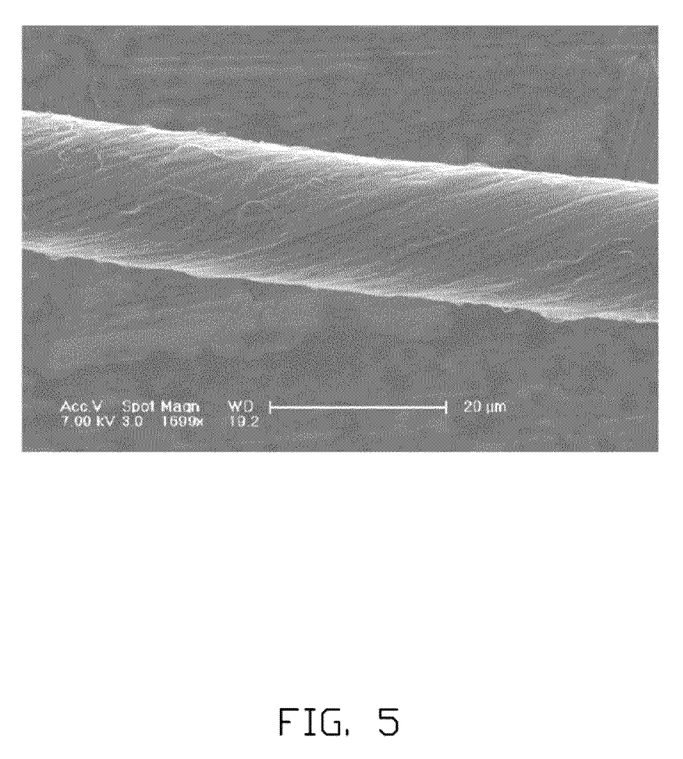
FIG. 5 is a SEM image of a twisted carbon nanotube wire.

Referring to FIGS. 3, 4, and 5, the carbon nanotube structure 12 can be at least one carbon nanotube film, at least one carbon nanotube wire, or a combination thereof. The carbon nanotube film can be a carbon nanotube drawn film. The carbon nanotube wire can be a non-twisted carbon nanotube wire or a twisted carbon nanotube wire. The carbon nanotube drawn film and the non-twisted carbon nanotube wire can be drawn out from a carbon nanotube array.

The carbon nanotube drawn film can be formed by the steps of: S(a), choosing a carbon nanotube segment having a predetermined width from a carbon nanotube array by a drawing tool; S(b), moving the drawing tool to pull the chosen carbon nanotube segment at a predetermined speed, thereby pulling out a continuous carbon nanotube drawn film including a plurality of carbon nanotube segments joined end-to-end by van der Waals attractive force therebetween. In step S(a), the drawing tool can be an adhesive tape or a rigid strip. The carbon nanotube segment includes a plurality of parallel carbon nanotubes arranged side by side. In step S(b), when the chosen carbon nanotube segment is pulled away from a grown substrate of the carbon nanotube array along a pulling direction, the adjacent carbon nanotube segment is pulled out from the carbon nanotube array due to van der Waals attractive force. The carbon nanotube drawn film is continuous, uniform, and includes a plurality of carbon nanotubes arranged along a same direction.

The carbon nanotube drawn film can be a free-standing structure. The carbon nanotube drawn film includes a plurality of carbon nanotubes that can be arranged substantially parallel to a surface of the carbon nanotube drawn film. A large number of the carbon nanotubes in the carbon nanotube drawn film can be oriented along a preferred orientation, meaning that a large number of the carbon nanotubes in the carbon nanotube drawn film are arranged substantially along the same direction. An end of one carbon nanotube is joined to another end of an adjacent carbon nanotube arranged substantially along the same direction by van der Waals attractive force. A small number of the carbon nanotubes are randomly arranged in the carbon nanotube drawn film, and has a small if not negligible effect on the larger number of the carbon nanotubes in the carbon nanotube drawn film arranged substantially along the same direction. The carbon nanotubes oriented substantially along the same direction may not be perfectly aligned in a straight line, and some curve portions may exist. It can be understood that some carbon nanotubes located substantially side by side and oriented along the same direction in contact with each other cannot be excluded.

In addition, the carbon nanotube structure 12 can include at least two stacked and/or coplanar drawn carbon nanotube films, thereby forming the carbon nanotube structure having different areas or different thicknesses. A thickness of the carbon nanotube drawn film can be in a range from about 0.5 nanometers (nm) to about 100 micrometers (μm). When the plurality of carbon nanotube drawn films are stacked with each other, an angle α between the aligned directions of the carbon nanotubes in the adjacent carbon nanotube drawn films can be in a range from about 0° to about 90°.

The non-twisted carbon nanotube wire can be formed by pulling a narrow carbon nanotube drawn film directly or cutting a wide carbon nanotube drawn film into a plurality of narrow carbon nanotube drawn films. The wide carbon nanotube drawn film can be cut along a lengthwise direction of the carbon nanotubes therein by using a laser beam. The non-twisted carbon nanotube wire includes a plurality of carbon nanotubes combined with each other by van der Waals attractive force and is a free-standing structure. The plurality of carbon nanotubes can be oriented along a preferred orientation, meaning that a large number of the carbon nanotubes in the non-twisted carbon nanotube wire are arranged substantially along the same direction. Extending directions of a large number of the carbon nanotubes in the non-twisted carbon nanotube wire are substantially parallel to the extending direction of the non-twisted carbon nanotube wire. In addition, the adjacent carbon nanotubes along the extending directions of the carbon nanotubes are joined end to end by van der Waals attractive force. A small number of the carbon nanotubes are randomly arranged in the non-twisted carbon nanotube wire, and has a small if not negligible effect on the larger number of the carbon nanotubes in the non-twisted carbon nanotube wire arranged substantially along the same direction. A diameter of the non-twisted carbon nanotube wire can be in a range from about 0.5 nm to about 100 μm.

More specifically, the non-twisted carbon nanotube wire includes a plurality of successive carbon nanotube segments joined end to end by van der Waals attractive force therebetween. Each carbon nanotube segment includes a plurality of carbon nanotubes substantially parallel to each other, and combined by van der Waals attractive force therebetween. The carbon nanotube segments can vary in width, thickness, uniformity and shape. Length of the non-twisted carbon nanotube wire can be arbitrarily set as desired.

The twisted carbon nanotbue wire is formed by twisting a carbon nanotube drawn film by using a mechanical force to turn the two ends of the carbon nanotube drawn film in opposite directions. The twisted carbon nanotube wire includes a plurality of carbon nanotubes oriented around an axial direction of the twisted carbon nanotube wire. The carbon nanotubes are aligned around the axis of the twisted carbon nanotube wire like a helix.

The above carbon nanotube film and the carbon nanotube wire are free-standing structures. The term "free-standing structure" includes, but is not limited to, a structure that does not need to be supported by a substrate. For example, a free-standing structure can sustain the weight of itself when it is hoisted by a portion thereof without any significant damage to its structural integrity. So, if the carbon nanotube film or the carbon nanotube wire are placed between two separate supporters, a portion of the carbon nanotube film or the carbon nanotube wire, not in contact with the two supporters, would be suspended between the two supporters and yet maintain film or wire structural integrity. The free-standing structure of the carbon nanotube film or the carbon nanotube wire is realized by the successive carbon nanotubes joined end to end by van der Waals attractive force.

In step S2, the conductive material can be combined with the carbon nanotube structure 12 by a physical method or a chemical method. The physical method can be a physical vapor deposition method such as a vacuum evaporation method or an ion sputtering method. The chemical method can be an electroplating method or a chemical plating method. In one embodiment, the conductive material is combined with the carbon nanotube film by vacuum evaporation method.

Figure 6:
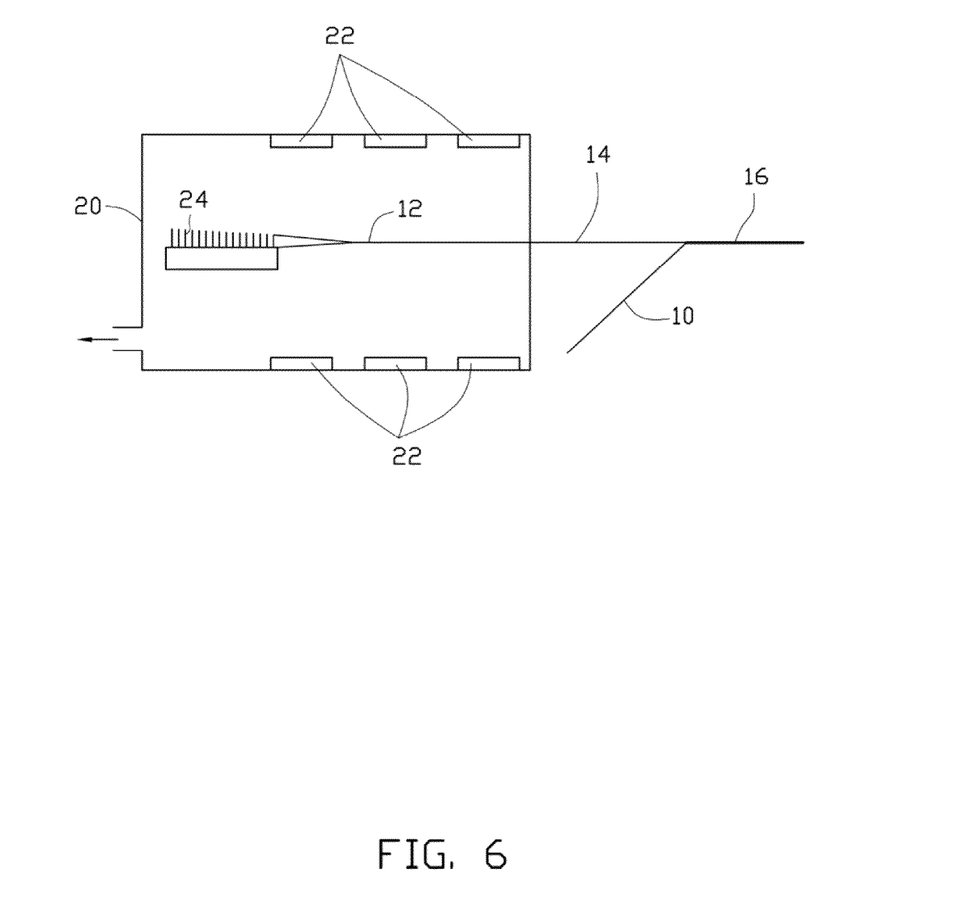
FIG. 6 is a schematic view of the method of FIG. 1.

Referring to FIG. 6, the vacuum evaporation method for forming the carbon nanotube composite structure 14 can include the following steps of: S21, providing a vacuum container 20 including at least one vaporizing source 22; and S22, heating the at least one vaporizing source 22 to deposit the conductive material on a surface of the carbon nanotube film.

In step S21, the vacuum container 20 includes a depositing zone therein. At least one pair of vaporizing sources 22 includes an upper vaporizing source located on a top surface of the depositing zone, and a lower vaporizing source located on a bottom surface of the depositing zone. The two vaporizing sources 22 are opposite to each other to provide the desired coverage. Each pair of vaporizing sources 22 includes a type of metallic material. The materials in different pairs of vaporizing sources 22 can be arranged in the order of conductive materials formed on the carbon nanotube film. The pairs of vaporizing sources 22 can be arranged along a pulling direction of the carbon nanotube film facing upper and lower surfaces of the carbon nanotube film. The carbon nanotube film is located in the vacuum container 20 and between the upper vaporizing source and the lower vaporizing source.

There is a distance between the carbon nanotube film and the vaporizing sources 22. The vacuum container 20 can be evacuated by use of a vacuum pump (not shown).

Figure 7:
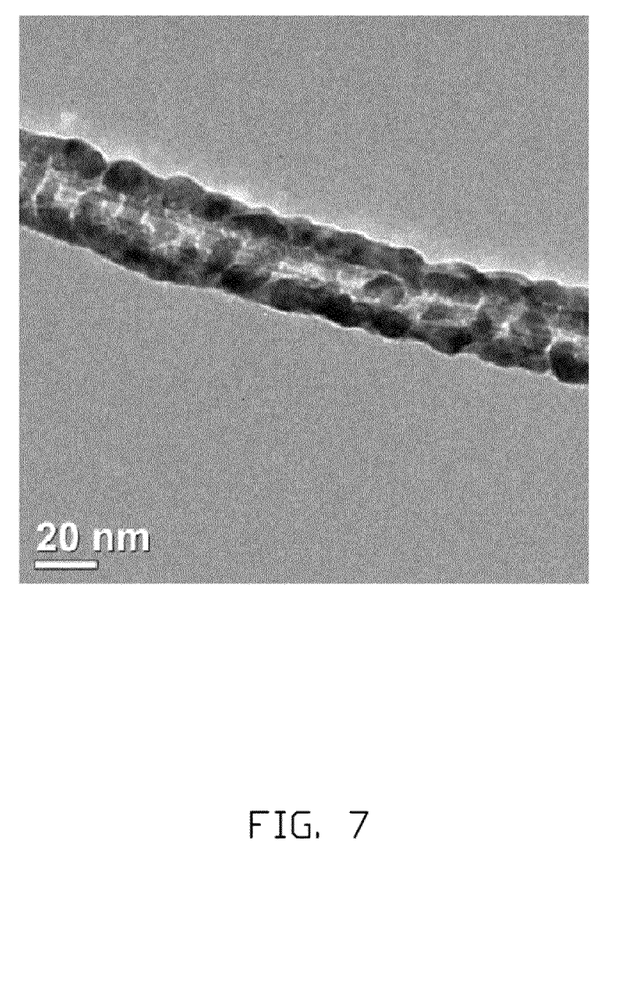
FIG. 7 is a transmission electron microscope (TEM) image of a carbon nanotube combined with a conductive material in a carbon nanotube composite structure.

In the step S22, the vaporizing source 22 can be heated by a heating device (not shown). The material in the vaporizing source 22 is vaporized or sublimed to form a gas. The gas meets the cold carbon nanotube film and coagulates on the upper surface and the lower surface of the carbon nanotube film. Due to a plurality of interspaces existing between the carbon nanotubes in the carbon nanotube film, and to the carbon nanotube film being relatively thin, the conductive material can infiltrate in the interspaces between the carbon nanotubes in the carbon nanotube film. As such, the conductive material can be deposited on the circumferential surface of most, if not all, of a single carbon nanotube. A microstructure of the carbon nanotube of the carbon nanotube composite structure 14 is shown in FIG. 7.

A depositing area of each vaporizing source 22 can be adjusted by varying the distance between two adjacent vaporizing sources 22 or the distance between the carbon nanotube film and the vaporizing source 22. If multilayered conductive materials needs to be deposited on the surface of the carbon nanotube film, several pairs of vaporizing sources 22 can be heated simultaneously and the carbon nanotube film can be continuously pulled through the depositing zone between the vaporizing sources 22.

To increase a density of the gas in the depositing zone, and prevent oxidation of the conductive material, the vacuum degree in the vacuum container 20 can be less than 1 pascal (Pa). In one embodiment, the vacuum degree is about $4 \times 10^{-4}$ Pa.

The carbon nanotube array 24 in step S(a) can be directly placed in the vacuum container 20. The carbon nanotube structure 12 (e.g. carbon nanotube drawn film) can be pulled out from the carbon nanotube array 24 in the vacuum container 20 and continuously pass each vaporizing source 22, with each conductive material continuously depositing thereon. Thus, the pulling step and the depositing step can be processed simultaneously.

The method for forming the conductive material can include the following steps of: forming a wetting layer on two opposite surfaces of the carbon nanotube film; forming a transition layer on the wetting layer; and forming a conductive layer on the transition layer. In the above-described method, the steps of forming the wetting layer and the transition layer are optional. In one embodiment, the method for forming the conductive material includes the following steps: forming the wetting layer on two opposite surfaces of the carbon nanotube film; forming the transition layer on the wetting layer; and forming the conductive layer on the transition layer. In the formed carbon nanotube composite structure 14, the wetting layer, the transition layer, and the conductive layer are covered on the circumferential surface of the carbon nanotube one by one in the carbon nanotube composite structure 14.

Figure 8:
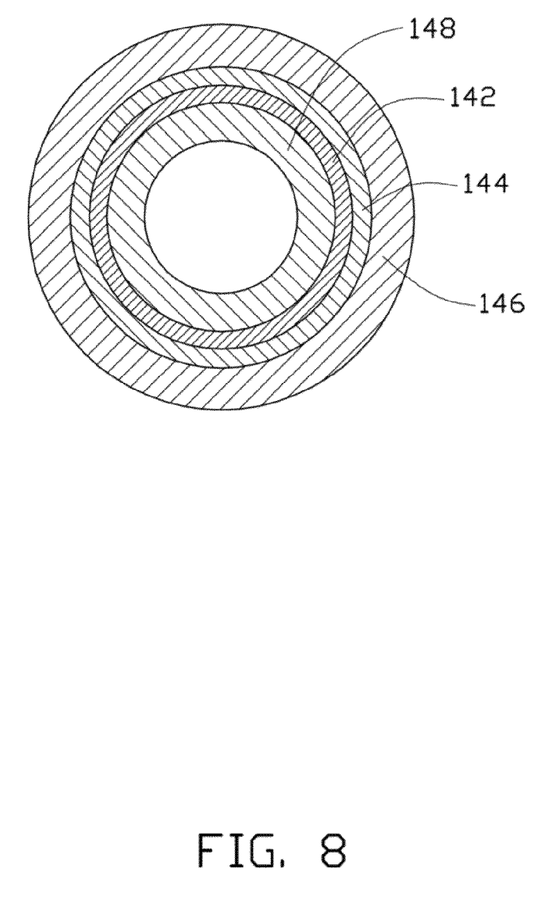
FIG. 8 is a structural schematic view of the carbon nanotube combined with the conductive material in the carbon nanotube composite structure.

Referring to FIG. 8, each carbon nanotube 148 in the carbon nanotube composite structure 14 is successively covered by the wetting layer 142, the transition layer 144 and the conductive layer 146. The conductive layer 146 is arranged for enhancing the conductivity of the carbon nanotube structure 12. A material of the conductive layer 146 can be at least one of Cu, Ag, Au, and alloys thereof. A thickness of the conductive layer 146 can be in a range from about 1 nm to about 20 nm. In one embodiment, the material of the conductive layer 146 is Au and the thickness is about 2 nm. The carbon nanotube 148 cannot be adequately wetted by most metallic materials. Thus, the wetting layer 142 is arranged for wetting the carbon nanotube 148, as well as combining the carbon nanotube 148 with the conductive layer 146. A material of the wetting layer 142 can be at least one of iron (Fe), cobalt (Co), nickel (Ni), palladium (Pd), Ti, and alloys thereof. A thickness of the wetting layer 142 can be in a range from about 1 nm to about 10 nm. In one embodiment, the material of the wetting layer 142 is Ni and the thickness is about 2 nanometers. The wetting layer 142 is optional. The transition layer 144 is arranged for combining the wetting layer 142 with the conductive layer 146. A material of the transition layer 144 can be combined with both the material of the wetting layer 142 and the material of the conductive layer 146, such as Cu, Ag, or alloys thereof. A thickness of the transition layer 144 can be in a range from about 1 nm to about 10 nm. In one embodiment, the material of the transition layer 144 is Cu and the thickness is about 2 nm. The transition layer 144 is optional.

In addition, the ion sputtering method for combining the conductive material with the carbon nanotube film can include the steps of: suspending the carbon nanotube film between a upper conductive metal target and a lower conductive metal target under a vacuum pressure condition, wherein there is a distance between the carbon nanotube film and the conductive metal target; bombarding the upper conductive metal target and the lower conductive metal target with ionized cations under an electric field, thereby sputtering the conductive metal atoms on the two opposite surfaces of the carbon nanotube film.

The conductive material can also be formed on the surface of the carbon nanotube wire by using the above method. In one embodiment, the conductive material can be directly deposited on the surface of the carbon nanotube wire. In one embodiment, the carbon nanotube film combined with the conductive material can be rolled up along a direction substantially perpendicular to the extending direction of the carbon nanotubes, thereby forming a wire shaped carbon nanotube composite structure including a plurality of carbon nanotubes coated by the conductive material and substantially parallel to each other. Furthermore, the wire shaped carbon nanotube composite structure can be formed by twisting the carbon nanotube film combined with the conductive material by using a mechanical force to turn the two ends of the carbon nanotube film combined with the conductive material in opposite directions, thereby forming a twisted wire shaped carbon nanotube composite structure.

In the carbon nanotube composite structure 14, the conductive material is coated on the outer surface of each carbon nanotube 148 of the carbon nanotube structure 12. A plurality of gaps are defined by the adjacent carbon nanotubes in the carbon nanotube structure 12, thus, the carbon nanotube structure 12 has a large specific surface area. In the embodiment having each carbon nanotube 148 coated by the conductive material, a plurality of gaps remain between the coated carbon nanotubes, thus, the carbon nanotube composite structure 14 also has a large specific surface area.

In the step S3, the carbon nanotube composite structure 14 can cover the conductive wire structure 10 by two modes: mode 1 and mode 2.

In mode 1, the carbon nanotube composite structure 14 can be wound on the surface of the conductive wire structure 10 in a helix manner. The carbon nanotubes joined end to end extend around the axis of the conductive wire structure 10. A thread pitch of the carbon nanotube composite structure 14 wound on the surface of the conductive wire structure 10 can be in a range from about 0 mm to about 5 mm. In one embodiment, the thread pitch of the carbon nanotube composite structure 14 is about 3 mm.

In mode 1, one end of the carbon nanotube composite structure 14 is fixed on the conductive wire structure 10. The conductive wire structure 10 is then rotated and simultaneously moved along an axial direction of the conductive wire structure 10, such that the carbon nanotube composite structure 14 is wound on the surface of the conductive wire structure 10 along the axial direction of the conductive wire structure 10 in a helix manner. The carbon nanotube composite structure 14 can also be extended along the axial direction of the conductive wire structure 10 while rotating the conductive wire structure 10, so that the carbon nanotube composite structure 14 is wound on the surface of the conductive wire structure 10 along the axial direction of the conductive wire structure 10 in a helix manner. In addition, the carbon nanotube composite structure 14 can be immobile or rotate along an opposite rotating direction of the conductive wire structure 10. The conductive wire structure 10 can be continuously fabricated in mode 1.

In one embodiment, one end of the carbon nanotube composite structure 14 is fixed on the conductive wire structure 10. The carbon nanotube composite structure 14 is then rotated around the conductive wire structure 10, and simultaneously moved along the axial direction of the conductive wire structure 10. The carbon nanotube composite structure 14 can also be extended along the axial direction of the conductive wire structure 10 while rotating the conductive wire structure 10.

In mode 2, the carbon nanotube composite structure 14 is rolled on the surface of the conductive wire structure 10, and the arrangement directions of the carbon nanotubes in the carbon nanotube composite structure 14 are substantially parallel to the axis of the conductive wire structure 10.

Specifically, one end of the carbon nanotube composite structure 14 can be fixed on the immobile conductive wire structure 10, with a length direction of the carbon nanotubes in the carbon nanotube composite structure 14 substantially parallel to the axial direction of the conductive wire structure 10. The carbon nanotube composite structure 14 is then rolled around the conductive wire structure 10 along a direction substantially perpendicular to the conductive wire structure 10. In mode 2, the carbon nanotube composite structure 14 can be a film structure. A length of the film structure along the arrangement direction of the carbon nanotubes is substantially equal to a length of the conductive wire structure 10. Thus, the conductive wire structure 10 can be completely coated by the carbon nanotube composite structure 14.

In the step S4, the conductive wire composite structure 16 can be immersed by a volatile organic solvent. The carbon nanotube composite structure 14 can be shrunk under a surface tension generated by volatilization of the organic solvent. Thus, the gaps between the carbon nanotubes coated by the conductive material can be shrunk, the carbon nanotube composite structure 14 can be compactly combined with the conductive wire structure 10, and a frictional force between the carbon nanotube composite structure 14 and the conductive wire structure 10 can be improved. The organic solvent can be ethanol, methanol, acetone, dichloroethane, or chloroform. In one embodiment, the organic solvent is ethanol.

In the step S5, the first insulating layer 18 can insulate the carbon nanotube composite structure 14 and the conductive wire structure 10 from human body. The first insulating layer 18 can be made of a biocompatible polymer such as silica gel, polyurethane, polyfluortetraethylene, or silicon rubber-polyurethane copolymers. In one embodiment, a material of the first insulating layer 18 is silica gel.

Furthermore, one end of the conductive wire composite structure 16 can be exposed out from the first insulating layer 18 to form an exposure portion exposed to human body. The exposure portion can be directly used as an electrode head to stimulate the organ of the human body. The conductive wire composite structure 16 can be used to transfer an impulse signal to the exposure portion. The impulse signal can stimulate the organ of the human body by the exposure portion.

In addition, if the conductive wire composite structure 16 does not have the exposure portion, an additional electrode head can be welded on one end of the conductive wire composite structure 16 to electrically connect with the conductive wire composite structure 16. The additional electrode head can be conoid shape, cylindrical shape, helix shape, or ring shape. A material of the electrode head can be the same as the material of the conductive wire composite structure 16. The electrode head can be made of metal material or alloy material with an excellent conductivity, such as platinum-iridium alloy or carbon nanotubes. A bio-compatibility porous material can be further coated on a surface of the electrode head. The porous material can increase a sensing area of the electrode head, thereby improving the sensitivity of the sensing efficiency of the pacemaker electrode lead 100.

In addition, steps S2 and S3 can be simultaneously processed to continuously fabricate the pacemaker electrode lead 100.

In the pacemaker electrode lead 100, the carbon nanotube composite structure 14 coating on the conductive wire structure 10 can improve the mechanical property and the ductility of the pacemaker electrode lead 100. If a pulling force is applied to the pacemaker electrode lead 100, the conductive wire structure 10 will be stretched. The carbon nanotube composite structure 14 has a large specific surface area. Thus, a large friction force exists between the carbon nanotube composite structure 14 and the conductive wire structure 10 during the pulling of the pacemaker electrode lead 100, and the friction force can prevent the conductive wire structure 10 from being pulled apart. The carbon nanotube structure 12 in the carbon nanotube composite structure 14 has excellent mechanical properties, such as ductility and conductivity, and the conductive material combined with the carbon nanotube structure 12 can improve the conductivity of the carbon nanotube composite structure 14. In addition, if the conductive wire structure 10 is pulled apart, the carbon nanotube composite structure 14 can also transfer the impulse signal to stimulate the organ of the human body or sense physiological signals of the human body. Thus, a life span of the pacemaker electrode lead 100 can be improved.

Figure 9:
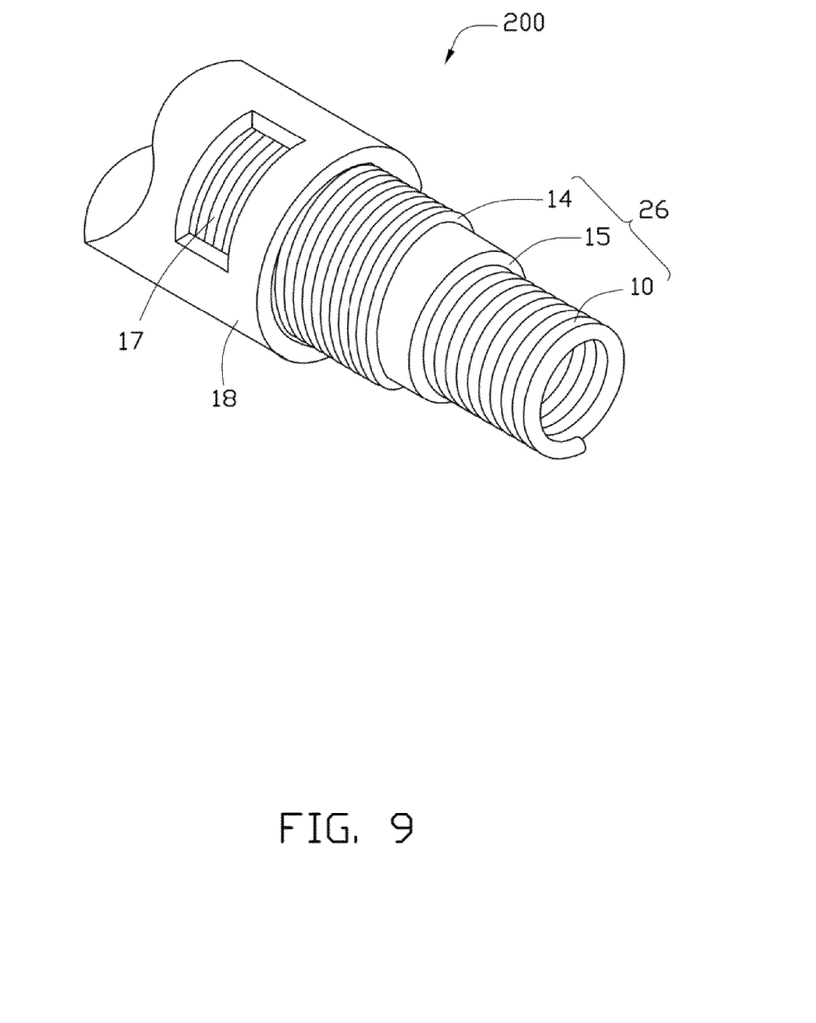
FIG. 9 is a schematic view of another embodiment of a pacemaker electrode lead made by another embodiment of a method.

Referring to FIG. 9, one embodiment of a method for making another embodiment of the pacemaker electrode lead 200 includes the following steps of:

M1, providing a conductive wire structure 10 and a carbon nanotube structure 12;

M2, combining a conductive material with the carbon nanotube structure 12 to form a carbon nanotube composite structure 14;

M3, coating a second insulating layer 15 on an outer surface of the conductive wire structure 10;

M4, covering the carbon nanotube composite structure 14 on an outer surface of the second insulating layer 15 to form a conductive wire composite structure 26;

M5, treating the conductive wire composite structure 26 using a volatile organic solvent; and M6, coating a first insulating layer 18 on an outer surface of the conductive wire composite structure 26.

Only step M3 is different from the above embodiment of the method for making the pacemaker electrode lead 100. In step M3, the conductive wire structure 10 and the carbon nanotube composite structure 14 are insulated from each other due to the second insulating layer 15. Thus, the conductive wire structure 10 and the carbon nanotube composite structure 14 can transfer different signals. Specifically, the conductive wire structure 10 can transfer an impulse signal to stimulate a human organ, and the carbon nanotube composite structure 14 can be used to sense a physiological signal of the human body. In addition, the conductive wire composite structure 26 is different from the conductive wire composite structure 16 made by the above embodiment, the conductive wire composite structure 26 further includes a second insulating layer 15.

A material of the second insulating layer 15 can be the same as or different from the material of the first insulating layer 18. The second insulating layer 15 can be made of biocompatible polymer such as silica gel, polyurethane, polyfluortetraethylene, or silicon rubber-polyurethane copolymers. In one embodiment, the material of the second insulating layer 15 is silica gel.

In addition, in step M3, one end of the conductive wire structure 10 can be exposed out from the second insulating layer 15 to form an exposure portion exposed to the human body. The exposure portion can be directly used as an electrode head to stimulate the organ of the human body. The conductive wire structure 10 can be used to transfer an impulse signal to the exposure portion. The impulse signal can stimulate the organ of the human body by the exposure portion. Thus, the exposure portion is only composed of one end of the conductive wire structure 10.

In the step M6, a bareness portion 17 can be further formed by exposing a portion of the carbon nanotube composite structure 14 from the first insulating layer 18 along an extending direction of the conductive wire structure 10. The bareness portion 17 can sense the physiological signal of the human body. The bareness portion 17 can be spaced from and near the exposure portion. A spacing distance between the bareness portion 17 and the exposure portion can be in a range from about 2 cm to about 10 cm. Furthermore, a plurality of bareness portions 17 can be formed along the extending direction of the conductive wire structure 10. The adjacent bareness portions 17 are spaced from each other. The bareness portion 17 can be formed by removing a portion of the first insulating layer 18.

The carbon nanotube composite structure 14 coating on the second insulating layer 15 can improve the mechanical property and the ductility of the electrode lead. If a pulling force is applied to the pacemaker electrode lead 200, the conductive wire structure 10 will be stretched. The carbon nanotube composite structure 14 has a large specific surface area. Thus, a large friction force exists between the carbon nanotube composite structure 14 and the second insulating layer 15 while pulling the pacemaker electrode lead 200, which can prevent the conductive wire structure 10 from being pulled apart.

It is to be understood, however, that even though numerous characteristics and advantages of certain inventive embodiments have been set out in the foregoing description, together with details of the structures and functions of the embodiments, the disclosure is illustrative only; and that changes may be made in detail, especially in matters of arrangement of parts within the principles of the present disclosure to the full extent indicated by the broad general meaning of the terms in which the appended claims are expressed.

What is claimed is:

1. A method for making a pacemaker electrode lead comprising:
   providing a conductive wire structure and a carbon nanotube structure, wherein the carbon nanotube structure comprises a plurality of carbon nanotubes substantially parallel with each other;
   combining a conductive material with the carbon nanotube structure to form a carbon nanotube composite structure;
   covering the carbon nanotube composite structure on a surface of the conductive wire structure to form a conductive wire composite structure; and
   treating the conductive wire composite structure by using a volatile organic solvent.

2. The method of claim 1, wherein the conductive wire structure is a hollow cylindrical structure or a solid columnar structure.

3. The method of claim 2, wherein a material of the conductive wire structure is selected from the group consisting of stainless steel, carbon fiber, Ta, Ti, Zr, Nb, titanium alloy, Cu, Ag, Pt, platinum yttrium alloy, platinum palladium alloy, and any combination thereof.

4. The method of claim 1, wherein the carbon nanotube structure is formed by pulling a carbon nanotube segment from a carbon nanotube array, the carbon nanotube structure comprises a plurality of carbon nanotubes extending along a same direction and joined end to end by van der Waals attractive force.

5. The method of claim 1, wherein the step of covering the carbon nanotube composite structure on the surface of the conductive wire structure is winding the carbon nanotube composite structure on the surface of the conductive wire structure in a helix manner, wherein the carbon nanotubes in the carbon nanotube composite structure are joined end to end by van der Waals attractive force and extend around an axis of the conductive wire structure.

6. The method of claim 5, wherein the step of winding the carbon nanotube composite structure on the surface of the conductive wire structure in a helix manner comprises: fixing one end of the carbon nanotube composite structure on the conductive wire structure; rotating the conductive wire structure and simultaneously moving the conductive wire structure along an axis of the conductive wire structure, or extending the carbon nanotube composite structure along the axial direction of the conductive wire structure while rotating the conductive wire structure.

7. The method of claim 5, wherein the step of winding the carbon nanotube composite structure on the surface of the conductive wire structure in a helix manner comprises: fixing one end of the carbon nanotube composite structure on the surface of the conductive wire structure; rotating the carbon nanotube composite structure around the conductive wire structure and simultaneously moving the conductive wire structure along an axial direction of the conductive wire structure or extending the carbon nanotube composite structure along the axial direction of the conductive wire structure while rotating the conductive wire structure.

8. The method of claim 1, wherein the step of covering the carbon nanotube composite structure on the surface of the conductive wire structure is rolling the carbon nanotube composite structure on the surface of the conductive wire structure, and an arrangement direction of the carbon nanotubes in the carbon nanotube composite structure are substantially parallel to an axis of the conductive wire structure.

9. The method of claim 1, wherein the conductive material is formed on a outer surface of each carbon nanotube of the carbon nanotube structure.

10. The method of claim 1, wherein the conductive material is combined with the carbon nanotube structure by vacuum evaporation method, ion sputtering method, electroplating method, or chemical plating method.

11. The method of claim 1, wherein the step of combining the conductive material with the carbon nanotube structure comprises: forming a conductive layer on a surface of the carbon nanotube structure.

12. The method of claim 11, wherein a material of the conductive layer is selected from the group consisting of Cu, Ag, Au, and alloys thereof.

13. The method of claim 11, wherein the step of combining the conductive material with the carbon nanotube structure further comprises: forming a wetting layer on the surface of the carbon nanotube structure before forming the conductive layer, wherein the conductive layer is formed on a surface of the wetting layer.

14. The method of claim 13, wherein the step of combining the conductive material with the carbon nanotube structure further comprises: forming a transition layer between the wetting layer and the conductive layer.

15. The method of claim 1, further comprising forming a first insulating layer to coat the conductive wire composite structure.

16. The method of claim 15, further comprising forming a second insulating layer between the conductive wire structure and the carbon nanotube composite structure.

17. The method of claim 16, further comprising exposing one end of the conductive wire structure from the carbon nanotube composite structure, the first insulating layer, and the second insulating layer.

18. The method of claim 17, further comprising exposing a portion of the carbon nanotube composite structure from the first insulating layer.

* * * * *